United States Patent
Okumura

(10) Patent No.: US 10,849,577 B2
(45) Date of Patent: Dec. 1, 2020

(54) RADIATION IMAGING APPARATUS AND RADIATION IMAGING SYSTEM

(71) Applicant: CANON KABUSHIKI KAISHA, Tokyo (JP)

(72) Inventor: Toshiaki Okumura, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 193 days.

(21) Appl. No.: 16/027,636

(22) Filed: Jul. 5, 2018

(65) Prior Publication Data

US 2019/0008469 A1  Jan. 10, 2019

(30) Foreign Application Priority Data

Jul. 10, 2017 (JP) .................................. 2017-134954

(51) Int. Cl.
*A61B 6/00* (2006.01)

(52) U.S. Cl.
CPC .............. *A61B 6/4283* (2013.01); *A61B 6/46* (2013.01); *A61B 6/486* (2013.01)

(58) Field of Classification Search
CPC ....... A61B 6/025; A61B 6/032; A61B 6/4007; A61B 6/4028; A61B 6/4405; A61B 6/547; A61B 6/4233; A61B 6/46; A61B 6/486
See application file for complete search history.

(56) References Cited

U.S. PATENT DOCUMENTS

| 6,285,738 | B1* | 9/2001 | Nagai | A61B 6/4225 |
| | | | | 378/98.3 |
| 7,664,222 | B2 | 2/2010 | Jabri et al. | |
| 2002/0080921 | A1* | 6/2002 | Smith | A61B 6/0457 |
| | | | | 378/189 |
| 2004/0258204 | A1* | 12/2004 | Nokita | A61B 6/00 |
| | | | | 378/91 |
| 2005/0135558 | A1* | 6/2005 | Claus | A61B 6/02 |
| | | | | 378/42 |
| 2010/0054399 | A1* | 3/2010 | Nishino | A61B 6/4233 |
| | | | | 378/28 |
| 2014/0254760 | A1* | 9/2014 | Hiroike | A61B 6/4233 |
| | | | | 378/62 |
| 2016/0073998 | A1* | 3/2016 | Shima | A61B 6/4476 |
| | | | | 378/64 |
| 2016/0157810 | A1* | 6/2016 | Tezuka | A61B 6/54 |
| | | | | 378/91 |
| 2016/0166227 | A1* | 6/2016 | Tanaka | A61B 6/563 |
| | | | | 382/132 |

FOREIGN PATENT DOCUMENTS

| JP | 2008-253762 A | 10/2008 |
| JP | 2015-508011 A | 3/2015 |
| WO | 2013/126502 A | 8/2013 |

* cited by examiner

*Primary Examiner* — Chih-Cheng Kao
(74) *Attorney, Agent, or Firm* — Venable LLP

(57) ABSTRACT

A radiation imaging apparatus in which a detection unit configured to generate an image signal corresponding to incident radiation and a control unit are arranged in one housing is provided. The radiation imaging apparatus further comprises a notification unit arranged in the housing and configured to show a state of the radiation imaging apparatus. While causing the detection unit to perform a continuous capturing operation of a radiation image, the control unit performs control so that the notification unit will perform notification of the ongoing capturing operation.

17 Claims, 10 Drawing Sheets

RADIATION IMAGING APPARATUS AND RADIATION IMAGING SYSTEM

BACKGROUND OF THE INVENTION

Field of the Invention

The present invention relates to a radiation imaging apparatus and a radiation imaging system.

Description of the Related Art

In a medical image diagnosis, a radiation imaging apparatus that uses a flat panel detector (FPD) formed by semiconductor materials is widely used. Along with the improvement in the performance of the driving circuit which is mounted in an FPD, a radiation imaging apparatus capable of a continuous capturing operation, including a moving image capturing operation, has become commercially available and is used for imaging methods such as tomosynthesis. In addition, along with miniaturization and power savings in electronic circuits and the development of wireless techniques used in a radiation imaging apparatus, a portable radiation imaging apparatus that can flexibly cope with various kinds of imaging situations has been put to practical use.

Japanese Patent Laid-Open No. 2015-508011 and Japanese Patent Laid-Open No. 2008-253762 each disclose a radiation imaging apparatus that is portable and capable of tomosynthesis imaging. Japanese Patent Laid-Open No. 2015-508011 and Japanese Patent Laid-Open No. 2008-253762 each disclose that the obtained image data is transferred by a wireless connection.

SUMMARY OF THE INVENTION

When a continuous capturing operation of a moving image or the like is performed, continuously captured radiation images may not be transferred in real time to a display device for displaying the captured radiation image due to the communication environment between a radiation imaging apparatus and the display device. In an environment in which a radiation image cannot be transferred in real time, it is difficult to determine whether the radiation imaging apparatus is capturing a radiation image.

The present invention provides a technique advantageous in allowing a user to recognize that a radiation image capturing operation is ongoing in a radiation imaging apparatus.

According to some embodiments, a radiation imaging apparatus in which a detection unit configured to generate an image signal corresponding to incident radiation and a control unit are arranged in one housing, wherein the radiation imaging apparatus further comprises: a notification unit arranged in the housing and configured to show a state of the radiation imaging apparatus, wherein while causing the detection unit to perform a continuous capturing operation of a radiation image, the control unit performs control so that the notification unit will perform notification of the ongoing capturing operation, is provided.

Further features of the present invention will become apparent from the following description of exemplary embodiments (with reference to the attached drawings).

DESCRIPTION OF THE EMBODIMENTS

Figure 1:
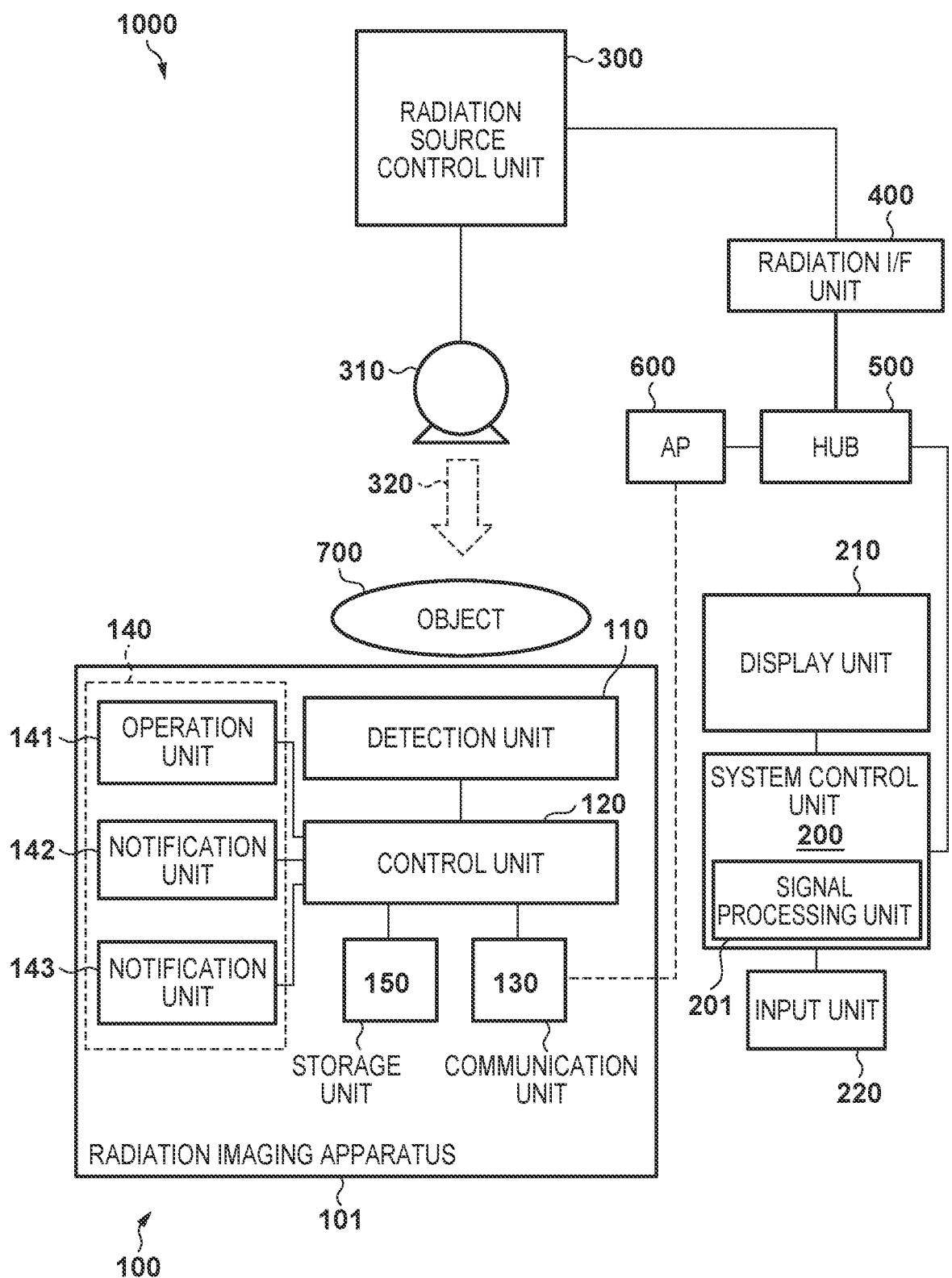
FIG. 1 is a view showing an example of the arrangement of a radiation imaging system using a radiation imaging apparatus according to an embodiment of the present invention.

A detailed embodiment of a radiation imaging apparatus according to the present invention will now be described with reference to the accompanying drawings. Note that in the following description and drawings, common reference numerals denote common components throughout a plurality of drawings. Hence, the common components will be described by cross-reference to the plurality of drawings, and a description of components denoted by common reference numerals will be appropriately omitted. Note that radiation according to the present invention can include not only α-rays, β-rays, and γ-rays that are beams generated by particles (including photons) emitted by radioactive decay but also beams having energy equal to or higher than the energy of these beams, for example, X-rays, particle beams, and cosmic rays.

The arrangement and operation of a radiation imaging apparatus according to an embodiment of the present invention will be described with reference to FIGS. 1 to 5. FIG. 1 is a view showing an example of a radiation imaging system 1000 using a radiation imaging apparatus 100 according the first embodiment of the present invention. The radiation imaging system 1000 includes the radiation imaging apparatus 100, a system control unit 200, and a radiation source 310 that irradiates the radiation imaging apparatus 100 with radiation via an object 700.

The radiation imaging apparatus 100 obtains an image signal for generating a radiation image of the object 700 based on radiation 320 which is emitted from the radiation source 310 and transmitted through the object 700.

As the radiation imaging apparatus 100, for example, a radiation imaging apparatus that uses a flat panel detector (FPD) is used. The radiation imaging apparatus 100 includes a control unit 120 and a detection unit 110 such as an FPD in a single housing 101. The detection unit 110 converts the radiation that has reached the detection unit into an electric signal. Each converted electric signal can be digitized and transmitted to the control unit 120 to undergo various kinds of processes and be subsequently transmitted to a storage unit 150 to be stored in a storage device such as a memory. The converted electric signal also can be transmitted to a communication unit 130 and transmitted, via a communication interface, to the system control unit 200 which is arranged outside the radiation imaging apparatus 100.

Other than image signal processing, the control unit 120 performs control of each component of the radiation imaging apparatus 100 such as driving of the detection unit 110, processing of user input to a user interface (user I/F) 140, and the like. The user I/F 140 includes an operation unit 141 and notification units 142 and 143. The notification units 142 and 143 are used to notify a user of the state of the radiation imaging apparatus 100. The notification units 142 and 143 each may be a display unit such as, for example, a light emitting diode (LED) or a liquid crystal display (LCD) that displays the state of the radiation imaging apparatus 100 by using at least one of a character, a figure, and light. The notification units 142 and 143 each may be a sound emitting unit such as, for example, a buzzer, a loudspeaker, and the like that indicates the state of the radiation imaging apparatus 100 by sound. The operation unit 141 is a unit used by the user to control the radiation imaging apparatus 100 such as the power on and off of the apparatus, and various kinds of switches and a touch panel can be used as the operation unit. Although the operation unit 141 is arranged in the radiation imaging apparatus 100 in the arrangement shown in FIG. 1, it may be arranged to a part other than the radiation imaging apparatus 100. The function of the operation unit 141 can be provided, for example, as a function of the system control unit 200. In this case, for example, the user may operate, from a menu displayed on a display unit 210 which is connected to the system control unit 200, an input unit 220 which is connected to the system control unit 200 to implement the function of the operation unit 141.

The system control unit 200 is a unit to control each arrangement of the radiation imaging system 1000 such as the operations and the imaging modes of the radiation imaging system 1000, the processing of each image signal captured by the radiation imaging apparatus 100, and the like. For example, various kinds of computers and work stations can be used as the system control unit 200. As described above, the display unit 210 such as a display for displaying a radiation image captured by the radiation imaging apparatus 100 and the input unit 220 such as a mouse and a keyboard for the user to perform various kinds of inputs can be connected to the system control unit 200. A signal processing unit 201 of the system control unit 200 processes each image signal transmitted from the radiation imaging apparatus 100, and the system control unit 200 displays a radiation image on the display unit 210.

The radiation source 310 can be formed by, for example, a rotor and an electron gun for generating the radiation 320. The radiation source 310 generates radiation when electrons emitted from the electron gun are accelerated by the high voltage generated in a radiation source control unit 300 and the accelerated electrons collide with the rotor.

In the arrangement shown in FIG. 1, communication between the radiation imaging apparatus 100 and the system control unit 200 is performed by a wireless LAN via an access point (AP) 600. However, the communication between the radiation imaging apparatus 100 and the system control unit 200 is not limited to this. For example, the communication between the radiation imaging apparatus 100 and the system control unit 200 may be directly performed, without the intervention of the AP 600, by causing one of the radiation imaging apparatus 100 and the system control unit 200 to be an access point. The communication between the radiation imaging apparatus 100 and the system control unit 200 may use another communication method such as Bluetooth®.

A radiation interface (I/F) unit 400 is arranged between the system control unit 200 and the radiation source control unit 300. The radiation I/F unit 400, which includes a circuit that mediates the communication between the radiation imaging apparatus 100 and the radiation source control unit 300, relays the exchange of synchronization signals and the like. The radiation I/F unit 400 can monitor the states of the radiation imaging apparatus 100 and the radiation source control unit 300, respectively, and adjust, for example, the irradiation timing of the radiation 320 from the radiation source 310 in accordance with the state of the radiation imaging apparatus 100. In addition, by also connecting the radiation source control unit 300 to the system control unit 200 via the radiation I/F unit 400, the exchange of various control signals and information can be relayed between the system control unit 200 and the radiation source control unit 300.

In the arrangement shown in FIG. 1, the radiation I/F unit 400 is connected to the system control unit 200 by Ethernet® via a HUB 500. The HUB 500 is a unit for connecting a plurality of network devices. By connecting the HUB 500 to the AP 600, the radiation I/F unit 400 is also connected to the radiation imaging apparatus 100 via the wireless LAN.

Figure 2:
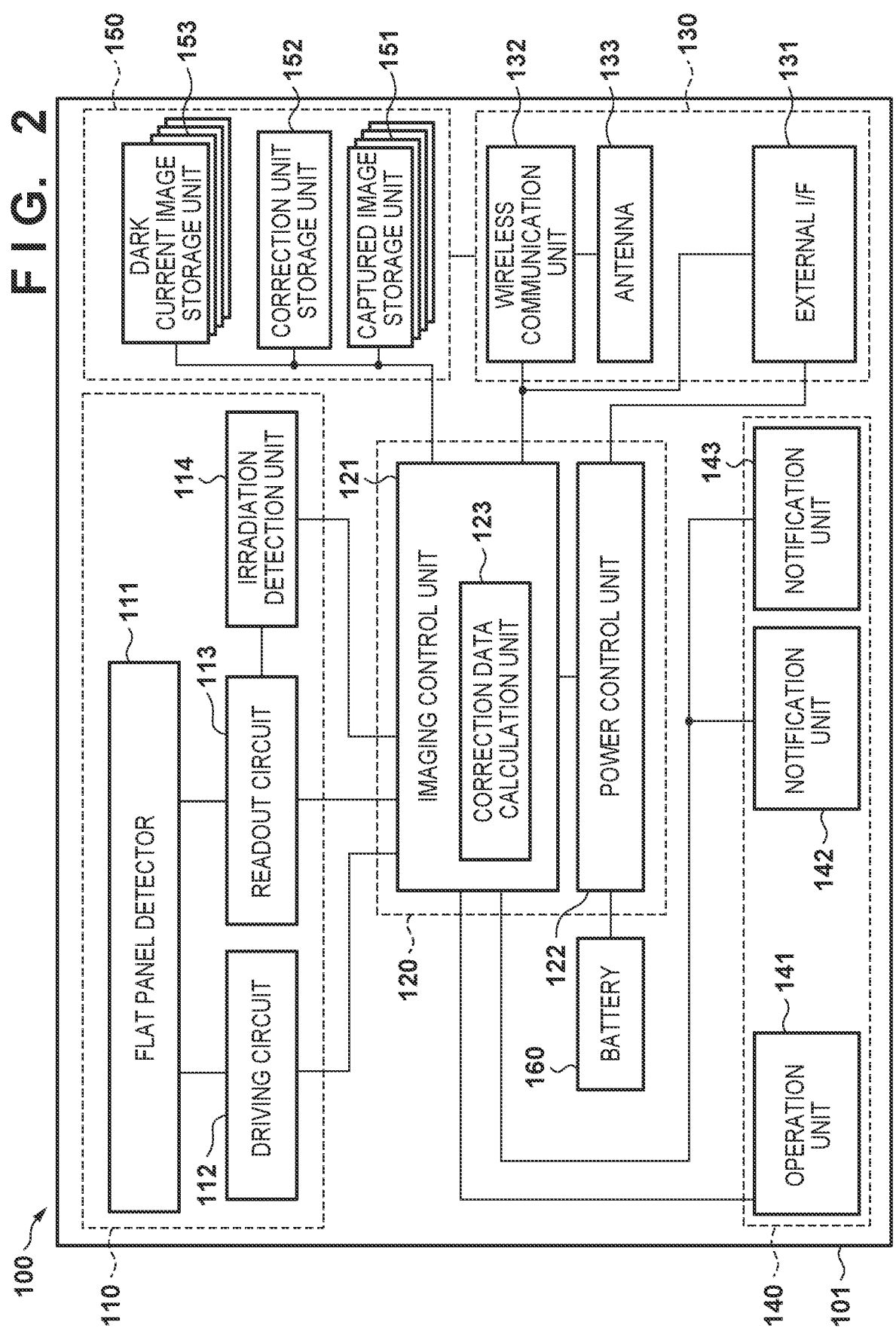
FIG. 2 is a block diagram showing an example of the arrangement of the radiation imaging apparatus of FIG. 1.

The arrangement of the radiation imaging apparatus 100 according to this embodiment will be described with reference to FIG. 2. FIG. 2 is a schematic view showing an example of the arrangement of the radiation imaging apparatus 100. The detection unit 110, the control unit 120, the communication unit 130, the user I/F 140, and the storage unit 150 are arranged in the single housing 101 of the radiation imaging apparatus 100.

The control unit 120 includes an imaging control unit 121 and a power control unit 122. The imaging control unit 121 is a unit for controlling the overall operation of the radiation imaging apparatus 100. The power control unit 122 is a unit to control the operation power of the radiation imaging apparatus 100. The power control unit 122 receives power from a battery 160 or an external interface (I/F) 131, generates various kinds of power necessary for the operation of the radiation imaging apparatus 100, and supplies the generated power to each unit forming the radiation imaging apparatus 100. The imaging control unit 121 may also include a function that controls the charging of the battery 160. That is, the radiation imaging apparatus 100 may be driven by external power supplied from the external I/F 131 or driven by power charged in the battery 160. The radiation imaging apparatus 100 can be used as a portable apparatus when it is driven by the power charged in the battery 160.

The imaging control unit 121 is connected to the detection unit 110. The detection unit 110 includes a flat panel detector 111, a driving circuit 112, a readout circuit 113, and an irradiation detection unit 114. The irradiation detection unit 114 detects that the radiation imaging apparatus 100 is being irradiated with radiation. For example, the imaging control unit 121 may use the irradiation detection unit 114 to detect the start of radiation irradiation and may start, in response to the detection, obtaining an image signal for generating a radiation image by using the flat panel detector 111. More specifically, the imaging control unit 121 transmits, to the irradiation detection unit 114 via the readout circuit 113, charges generated by the radiation irradiation to the flat panel detector 111 and detects the start of radiation irradiation by capturing changes in the current amount which is generated during the radiation irradiation operation. For example, the start of radiation irradiation can be detected by the imaging control unit 121 determining that the sample value of a signal input to the irradiation detection unit 114 has exceeded a predetermined threshold.

The imaging control unit 121 may perform various kinds of processes on each image signal generated by the flat panel detector 111 of the detection unit 110. Processes performed by the imaging control unit 121 are, for example, image processing operations that include loss correction due to fixed pattern noise of an image, offset correction, and processing to reduce various kinds of noise. However, all of the processes required for generating a final radiation image need not be performed in the imaging control unit 121, and it suffices to perform only the minimum required processing. The imaging control unit 121 need not perform processing on the image signal. The processing on the image signal may be performed by, for example, the signal processing unit 201 of the system control unit 200.

An image signal processed by the imaging control unit 121 is transmitted to the storage unit 150. The storage unit 150 includes a captured image storage unit 151. The captured image storage unit 151 is a unit for storing each image signal processed by the imaging control unit 121 together with various pieces of information that accompany the image signal. For example, a device such as a flash memory can be used as the captured image storage unit 151. Various pieces of information that accompany an image signal include, for example, information related to a patient who has been captured, information related to a user (an imaging technician, a doctor, or the like) who performed the capturing operation, and information such as a unique ID for image identification. A piece or a plurality of pieces of the information may be combined and linked to an image signal and stored. The storage unit 150 may also be used for storing an operation log of the radiation imaging apparatus 100. A correction unit storage unit 152 that saves the loss information used for image signal correction, fixed pattern noise information, and gain information and a dark current image storage unit 153 may be arranged in the storage unit 150 as shown in FIG. 2.

The communication unit 130 is arranged in the radiation imaging apparatus 100 so that the obtained image signal is transmitted to a device external to the radiation imaging apparatus 100 such as the system control unit 200. The communication unit 130 includes, the external I/F 131, a wireless communication unit 132, and an antenna 133. The wireless communication unit 132 is a unit for wirelessly transmitting, to the external system control unit 200, each image signal stored in the captured image storage unit 151 of the storage unit 150, and the antenna 133 is connected to the wireless communication unit. The image signal need not only be transmitted from the imaging control unit 121 to the wireless communication unit 132 via the storage unit 150. An image signal which has been processed in the imaging control unit 121 may be directly transmitted externally via the wireless communication unit 132. At this time, each image signal may be stored in the captured image storage unit 151 of the storage unit 150 in parallel to its transmission to the external device. The transmission of image data to the system control unit 200 can be performed by wired communication via the external I/F 131 without intervention of the wireless communication unit 132.

The user I/F 140 includes, as described above, the operation unit 141 for the user to make various kinds of operations to the radiation imaging apparatus 100 and the notification units 142 and 143 for notifying the user of the state of the radiation imaging apparatus 100. The operation unit 141 and the notification units 142 and 143 are connected to the imaging control unit 121 of the control unit 120.

Figure 3:
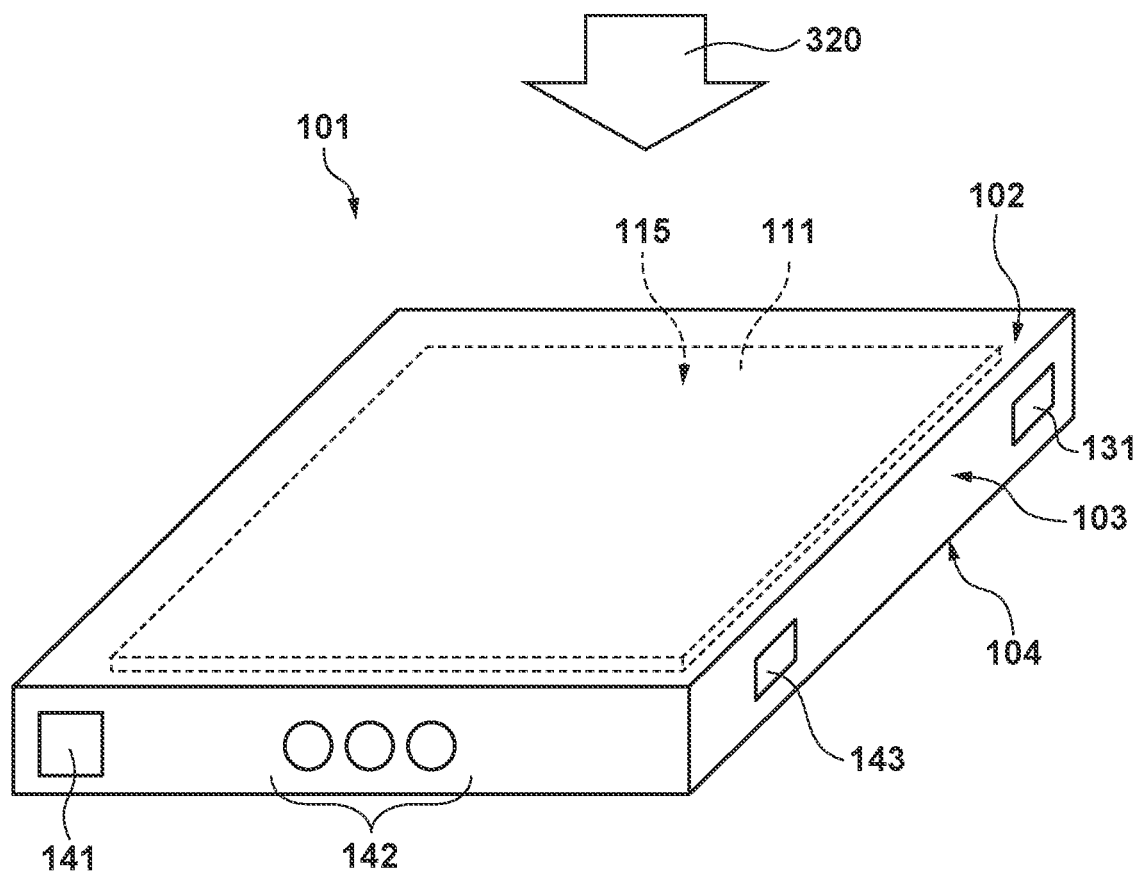
FIG. 3 is a schematic perspective view of the radiation imaging apparatus of FIG. 1.

FIG. 3 is a schematic view mainly showing the arrangement of a part related to the user I/F 140 of the radiation imaging apparatus 100 according to this embodiment. In the arrangement shown in FIG. 3, the housing 101 in which the user I/F 140 is arranged includes an incident surface 102 which is irradiated with the radiation 320, a back surface 104 on a side opposite to the incident surface 102, and side surfaces 103 set between the incident surface 102 and the back surface 104. The flat panel detector 111 of the detection unit 110 arranged inside the housing 101 includes a detection surface 115 on which a plurality of conversion elements for generating image signals corresponding to the incident radiation are arranged, and the detection surface 115 and the incident surface 102 are arranged so as to be parallel to each other.

On the side surfaces 103 of the housing 101 of the radiation imaging apparatus 100, the operation unit 141, the notification units 142 and 143, and the external I/F 131 are arranged. In this embodiment, the notification unit 142 is a display unit using LEDs and notifies the user of the state of the radiation imaging apparatus 100 by light. The number of LEDs used for the notification unit 142 is three in the arrangement of FIG. 3. However, the present invention is not limited to this, and the number of LEDs may be two or less or four or more. The number of LEDs may be appropriately set in accordance with the number of notification contents. In this embodiment, as shown in FIG. 3, by arranging the notification unit 142 on a surface on which the operation unit 141 is arranged among the side surfaces 103 of the housing 101, the user can intuitively determine the state of the radiation imaging apparatus 100 such as the power on/off of the radiation imaging apparatus 100. For example, the imaging control unit 121 of the control unit 120 may control the notification unit 142 so that the LEDs of the notification unit 142 are not turned on if the radiation imaging apparatus 100 is in a power-off state and so that the LEDs of the notification unit 142 light up in red upon changing to a power-on state. The notification unit 143 is an opening portion of the loudspeaker and notifies the user of the state of the radiation imaging apparatus 100 by sound.

The types of the notification units 142 and 143 are not limited to these, and a display unit such as an LCD and a buzzer may be used. The positions where the notification units 142 and 143 are arranged are not limited to the side surfaces 103 of the housing 101 of the radiation imaging apparatus 100. The notification units 142 and 143 may be arranged, for example, on the back surface 104 of the housing 101 of the radiation imaging apparatus 100 and on the incident surface 102 of the radiation imaging apparatus 100 as long as the units do not interfere with the imaging operation. The arrangement location of the display unit shown by the notification unit 142 is not limited to one location, and the display unit may be arranged in a plurality of locations so that the units can be easily visually recognized.

The operation unit 141 includes buttons, a dial, a slide switch, a touch sensor, and a touch pad, is an input interface for the user to perform various kinds of operations on the radiation imaging apparatus 100, and has a function of accepting instructions from the user. In this embodiment, a switch which functions as a power button of the radiation imaging apparatus 100 is arranged on the operation unit 141.

Figure 4A:
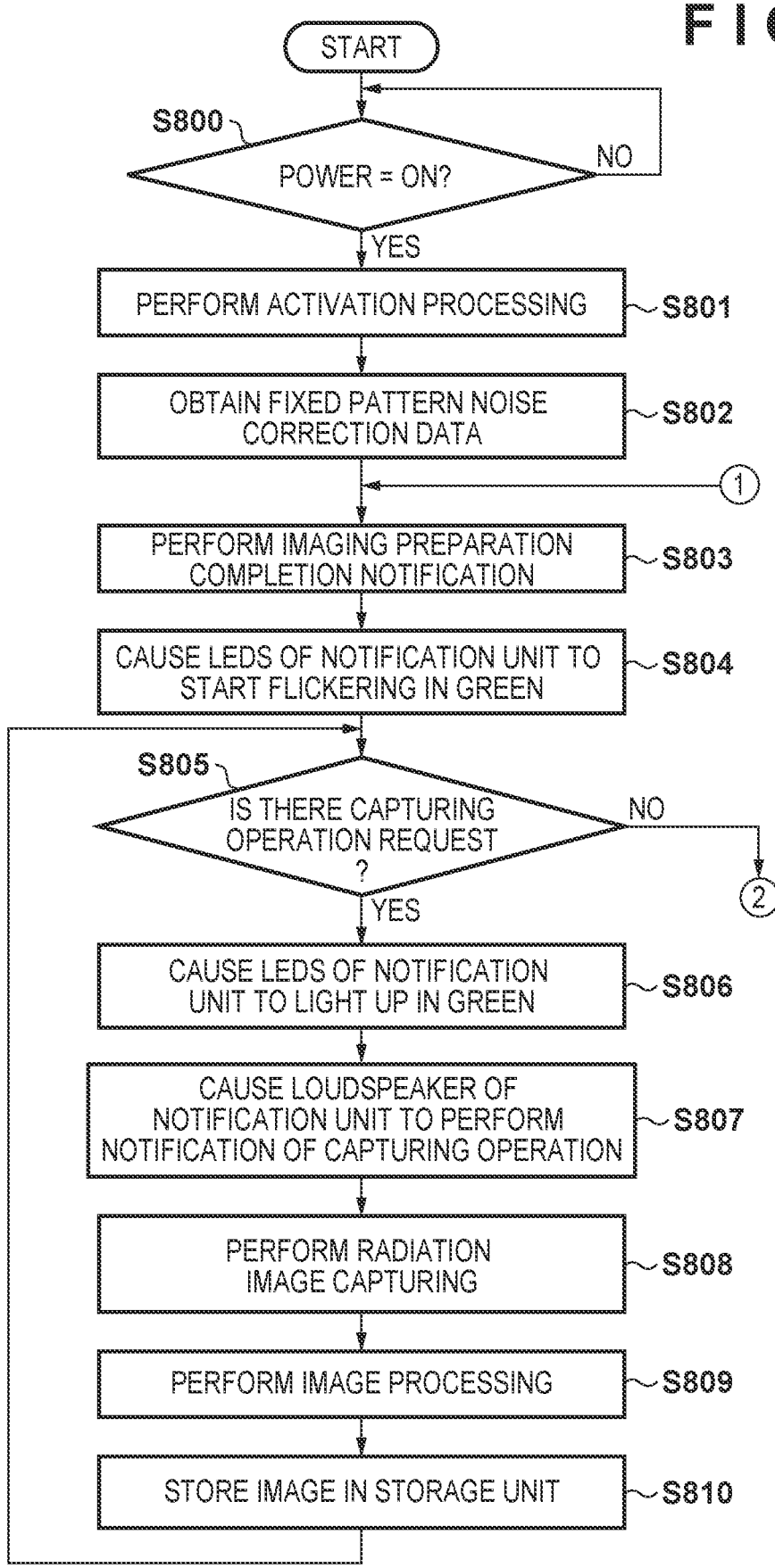
FIGS. 4A and 4B are flowcharts showing the procedure of an operation of the radiation imaging apparatus of FIG. 1.
Figure 4B:
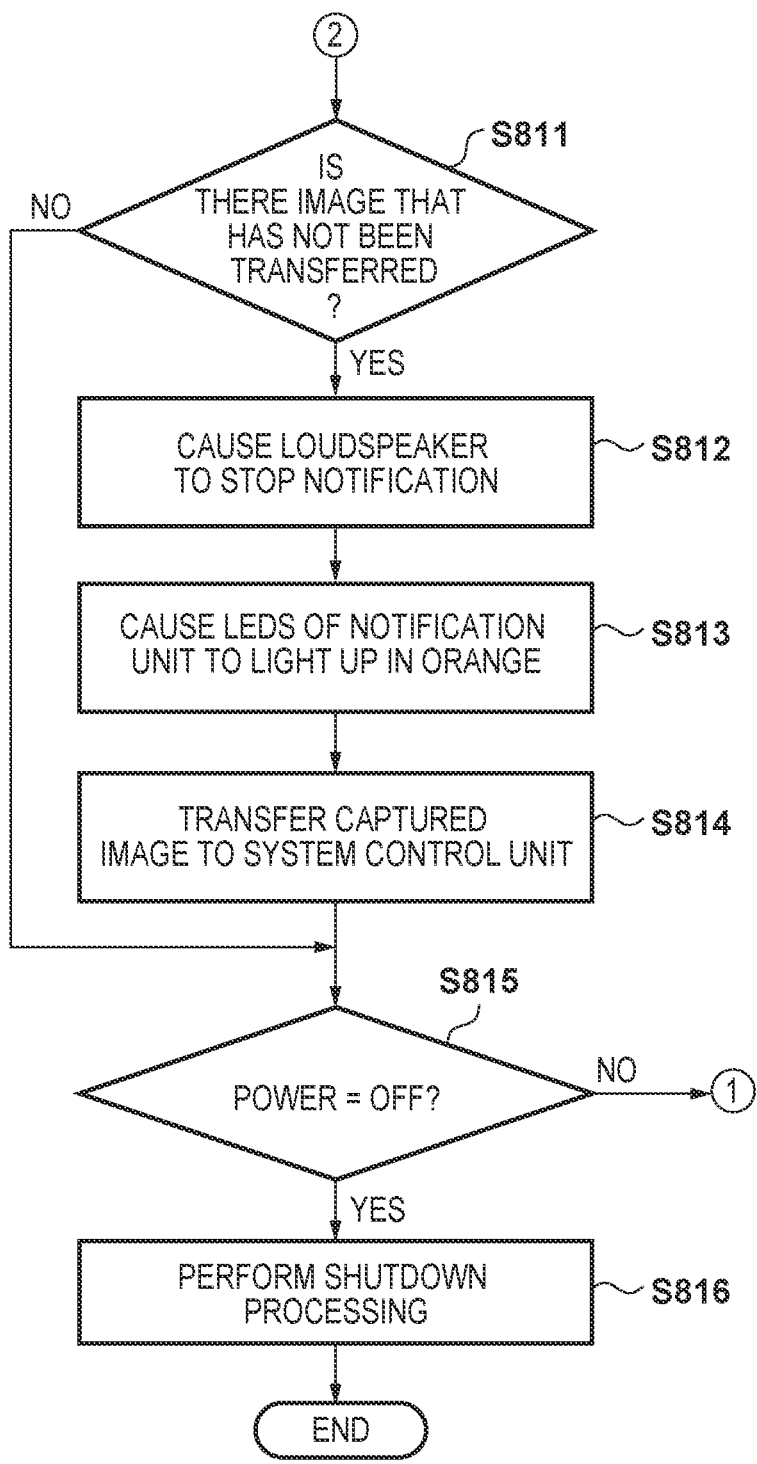

Next, the operation of the radiation imaging apparatus 100 according to this embodiment will be described in detail with reference to the operational flowchart of FIGS. 4A and 4B.

In this embodiment, the radiation imaging apparatus 100 has two power supply states, a power-off state and a power-on state. First, in a power-off state of the radiation imaging apparatus 100 in step S800, the radiation imaging apparatus stands by until the user presses the operation unit 141 which serves as the power button. Upon changing to the power-on state, the radiation imaging apparatus 100 shifts the process to step S801.

In step S801, the initial settings of the components are made for the imaging control unit 121, the wireless communication unit 132, the external I/F 131, the storage unit 150, and the detection unit 110 mounted in the radiation imaging apparatus 100. After making the initial settings, the radiation imaging apparatus 100 subsequently shifts process to step S802.

In step S802, the radiation imaging apparatus 100 first obtains, after changing to the power-on state, the fixed pattern noise correction data. The fixed pattern noise correction data is obtained by the imaging control unit 121 obtaining a dark current image by reading out dark current components accumulated in the respective pixels of the flat panel detector 111 by using the driving circuit 112 and the readout circuit 113. A plurality of these dark current images, for example, 30 images are obtained. The obtained dark current images are stored in the dark current image storage unit 153 of the storage unit 150. Next, a correction data calculation unit 123 of the imaging control unit 121 executes addition and averaging by using the dark current images stored in the dark current image storage unit 153 to create an average image of the dark current images. This average image is stored as the fixed pattern noise correction data in the correction unit storage unit 152 of the storage unit 150. The fixed pattern noise correction data may not only be obtained in step S802 immediately after changing to the power-on state, but also may be obtained and updated as necessary, for example, for each step in which the radiation imaging apparatus stands by for the notification of an exposure instruction signal (to be described later) or for each predetermined period. After the obtainment of the fixed pattern noise correction data, the radiation imaging apparatus 100 shifts the process to step S803.

In step S803, the radiation imaging apparatus 100 notifies the radiation source control unit 300 of the completion of the imaging preparation via the radiation I/F unit 400 and transits to step S804. In step S804, the imaging control unit 121 of the control unit 120 performs control so that the notification unit 142 will notify the user of the completion of the above-described initial settings in the detection unit 110 and the completion of the imaging preparation for capturing a radiation image. More specifically, the imaging control unit 121 of the control unit 120 performs control so that the LEDs of the notification unit 142 will start flickering in green. Next, the radiation imaging apparatus 100 shifts the process to step S805.

In step S805, the radiation imaging apparatus 100, having completed the imaging preparation, stands by for the notification of the exposure instruction signal which causes the radiation source 310 to emit the radiation 320. The exposure instruction signal notification is transmitted to the radiation imaging apparatus 100 from the radiation source control unit 300 via the radiation I/F unit 400 if the user presses an irradiation switch or a fluoroscopy pedal (not shown) which is connected to the radiation source control unit 300. If there is notification of the exposure instruction signal and the imaging control unit 121 of the control unit 120 starts to receive the exposure instruction signal, the radiation imaging apparatus 100 shifts the process to step S806. In a case in which there is no notification of the exposure instruction signal even after a predetermined standby time has elapsed, the radiation imaging apparatus 100 shifts the process to step S811.

In step S806, the imaging control unit 121 of the control unit 120 performs control, in response to receiving the exposure instruction signal in step S805, so that the detection unit 110 will start a continuous capturing operation of radiation images. This causes the radiation imaging apparatus 100 to shift to a continuous capturing operation such as moving image capturing. In response to this, in order to notify the user of the ongoing capturing operation, the imaging control unit 121 of the control unit 120 performs control so that the LEDs of the notification unit 142 will continuously light up in green. While causing the detection unit 110 to perform the radiation image capturing operation, the imaging control unit 121 of the control unit 120 performs control so that the notification unit 142 can notify the user of the ongoing continuous capturing operation by causing the LEDs of the notification unit 142 to continuously light up in green. In addition to notifying the user of the capturing operation by light in step S806, the imaging control unit 121 of the control unit 120 causes, in step S807, the loudspeaker of the notification unit 143 to continuously output a sound to notify the user of the execution of the continuous capturing operation. After the notifying the user, by using the notification units 142 and 143, that a radiation image capturing operation is being performed in the detection unit 110, the radiation imaging apparatus 100 shifts the process to step S808.

In step S808, the radiation imaging apparatus 100 performs a radiation image capturing operation by causing the imaging control unit 121 to synchronize with the irradiation timing of the radiation 320 emitted from the radiation source 310. After the obtainment of each radiation image, the radiation imaging apparatus 100 shifts the process to step S809.

In step S809, the radiation imaging apparatus 100 performs necessary image processing such as fixed pattern noise correction by the imaging control unit 121 on each image signal obtained by detection unit 110, and the radiation imaging apparatus shifts the process to step S810. In step S810, the radiation imaging apparatus 100 stores, in the captured image storage unit 151, the image signal that has undergone the necessary image processing by the imaging control unit 121.

In this manner, while the imaging control unit 121 of the control unit 120 receives the exposure instruction signal, the radiation imaging apparatus 100 repetitively performs the processes of the above-described steps S805 to S810 to perform a continuous capturing operation of an image including a moving image. Next, if the user has set the irradiation switch or the fluoroscopy pedal to OFF or if a capturing operation corresponding to a frame count designated by an imaging technique defined by the user before the capturing operation has been completed, the exposure instruction signal notification from the radiation source control unit 300 stops. The radiation source 310 stops the radiation irradiation in accordance with the suspension of the exposure instruction signal notification. Also, in response to the end of the exposure instruction signal notification, the imaging control unit 121 of the control unit 120 performs control to end the continuous capturing operation of the radiation image in the detection unit 110, and the radiation imaging apparatus 100 shifts the process to step S811.

In step S811, if an image signal is stored in the captured image storage unit 151 of the storage unit 150, the radiation imaging apparatus 100 determines that the capturing operation has ended and shifts the process to step S812. If an image signal is not stored in the captured image storage unit 151, the radiation imaging apparatus 100 shifts the process to step S815 by determining an exposure instruction signal notification standby state.

In step S812, to notify the user of the completion of the capturing operation, the radiation imaging apparatus 100 stops the sound which had been continuously emitted from the loudspeaker of the notification unit 143 and shifts the process to step S813.

In step S813, to notify the user that each image signal stored in the captured image storage unit 151 of the storage unit 150 is to be transferred to the system control unit 200 via the communication unit 130, the radiation imaging apparatus 100 causes the LEDs of the notification unit 142 to light up in orange. Next, the radiation imaging apparatus 100 shifts the process to step S814.

In step S814, the radiation imaging apparatus 100 transfers the image signals stored in the captured image storage unit 151 of the storage unit 150 to the system control unit 200 via the wireless communication unit 132 of the communication unit 130. While causing the communication unit 130 to output the image signals to the system control unit 200, the imaging control unit 121 of the control unit 120 controls the notification unit 142 to notify the user that the image signals are being output by causing the LEDs of the notification unit 142 to light up in orange. After the completion of the image signal transfer operation, the radiation imaging apparatus 100 shifts the process to step S815. In accordance with the shifting of the process to the step S815, the imaging control unit 121 of the control unit 120 controls the notification unit 142 so that the orange LEDs of the notification unit 142 are turned off.

In step S815, the radiation imaging apparatus 100 monitors whether the user will make an input to the power button which serves as the operation unit 141. If the user does not make an input to the power button and the radiation imaging apparatus 100 does not shift to the power-off state, the process shifts to step S803 as an exposure instruction signal notification standby state. After the process shifts to step S803, the imaging control unit 121 of the control unit 120 turns off the LEDs of the notification unit 142 and subsequently causes the LEDs of the notification unit 142 to light up in green in step S804.

In step S815, if the user makes an input to the power button and the radiation imaging apparatus 100 is to shift the process to the power-off state, the radiation imaging apparatus 100 shifts the process to step S816. In step S816, the radiation imaging apparatus 100 performs shutdown processing to change to the power-off state and ends the exposure instruction signal notification standby state.

Figure 5:
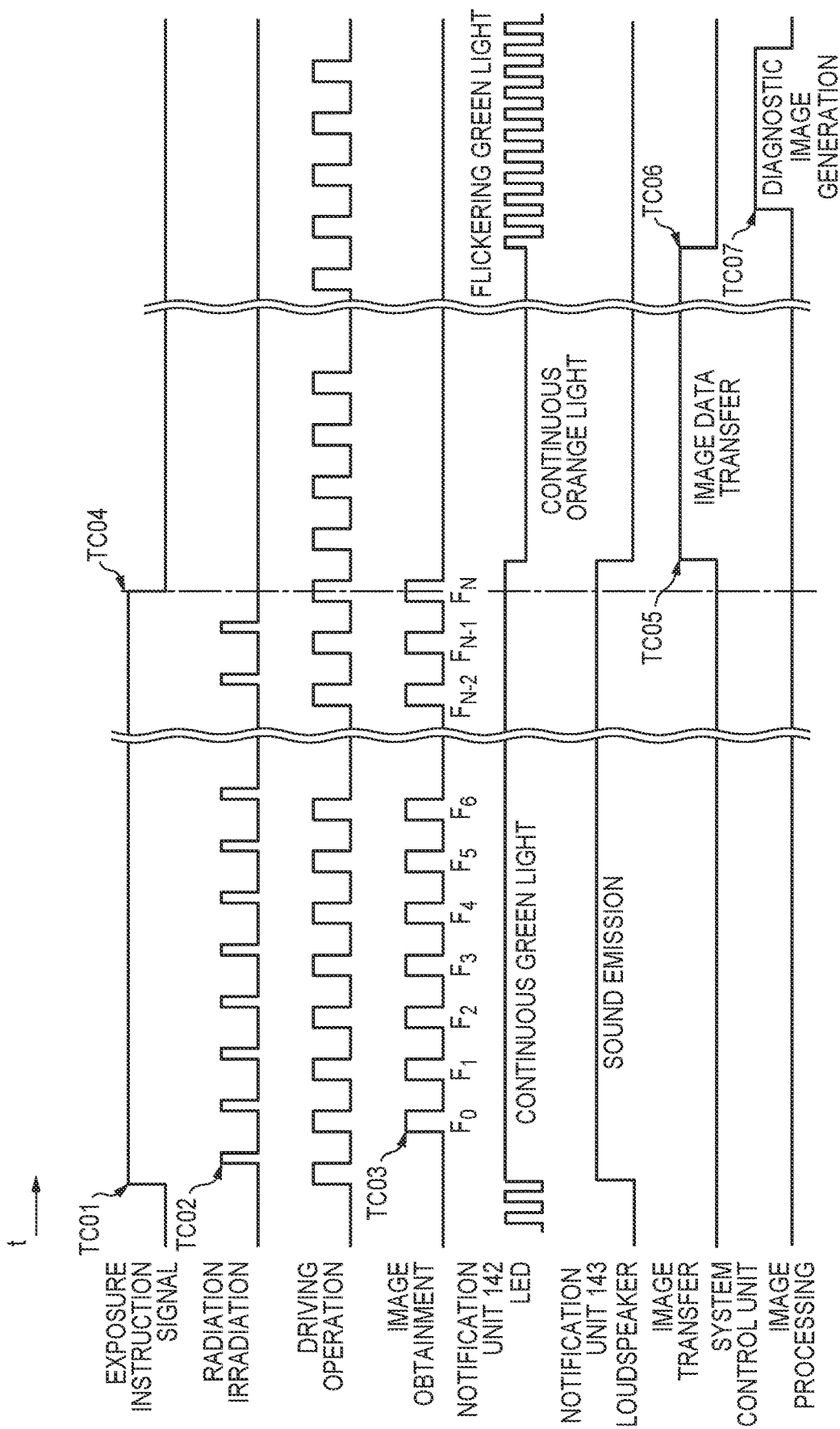
FIG. 5 is a timing chart showing the operation of the radiation imaging apparatus of FIG. 1.

FIG. 5 is a timing chart showing an example of the operation of the radiation imaging system 1000 which includes the radiation imaging apparatus 100, the radiation source control unit 300, and the system control unit 200 at the time of a continuous capturing operation according to this embodiment. Although the procedure of the operation according to this embodiment has been described with reference to FIGS. 4A and 4B, the operation of the radiation imaging system 1000 according to this embodiment will be described further with reference to a timing chart.

Upon receiving an exposure instruction signal notification (TC01) in a state in which the imaging preparation has been completed in the radiation imaging apparatus 100, the radiation source 310 starts radiation irradiation (TC02) in synchronization with the timing of the radiation imaging apparatus 100 by the control of the radiation source control unit 300. Although the arrangement of FIG. 5 shows that radiation irradiation is performed by performing pulse irradiation for each imaging frame to capture a radiation image, continuous radiation irradiation may be performed. The radiation imaging apparatus 100 that received the X-ray irradiation performs drive control by the control unit 120 at a predetermined timing and obtains (TC03) an image signal F0 corresponding to the radiation irradiation (TC02). The image signal obtained here is stored in the captured image storage unit 151 after undergoing necessary image processing such as fixed pattern noise correction.

Also, at the timing of the reception of the exposure instruction signal notification (TC01), the radiation imaging apparatus 100 changes the LEDs of the notification unit 142 from a flickering green light state, indicating that the imaging preparation is complete, to a continuous green light state, indicating that a radiation image continuous capturing operation is ongoing. The radiation imaging apparatus 100 simultaneously causes the loudspeaker of the notification unit 143 to continuously emit a sound. In this manner, the radiation imaging apparatus 100 repetitively performs the continuous capturing operation while notifying the user of the ongoing continuous capturing operation by using the LEDs of the notification unit 142 and the loudspeaker of the notification unit 143 until the exposure instruction signal notification ends (TC04).

After the completion of the continuous capturing operation (TC04), the radiation imaging apparatus 100 outputs (TC05) each image signal stored in the captured image storage unit 151 to the system control unit 200 via the imaging control unit 121 of the control unit 120, the wireless communication unit 132, and the antenna 133. During the image transfer operation, the radiation imaging apparatus 100 controls the LEDs of the notification unit 142 by the imaging control unit 121 of the control unit 120 so that the LEDs will light up in orange to indicate that the image is being transferred When the transfer of all of the image signals of the series of continuous capturing operations has been completed (TC06), the radiation imaging apparatus 100 changes to the imaging preparation completion state and performs control so that the LEDs of the notification unit 142 will be set to flickering green light display. As a result, the user can grasp whether the next continuous capturing operation can be performed.

When the reception of all of the image signals of the series of continuous capturing operations has been completed (TC06), the system control unit 200 performs signal processing on the image signals in the signal processing unit 201 and generates diagnostic image data (TC07). Here, for example, in the case of tomosynthesis imaging, the generation of diagnostic image data is performed by generating diagnostic image data that has been three-dimensionally reconstructed from the obtained sets of radiation image data which were captured from a plurality of positions.

In this manner, according to this embodiment, in a portable radiation imaging apparatus that has a high degree of freedom in imaging positions, can perform a continuous capturing operation, and performs wireless communication, display and a sound are used to perform notification of an ongoing continuous capturing operation such as moving image capturing or tomosynthesis imaging. As a result, a radiation imaging apparatus in which a user can easily recognize that a continuous capturing operation is being performed can be provided.

Figure 6:
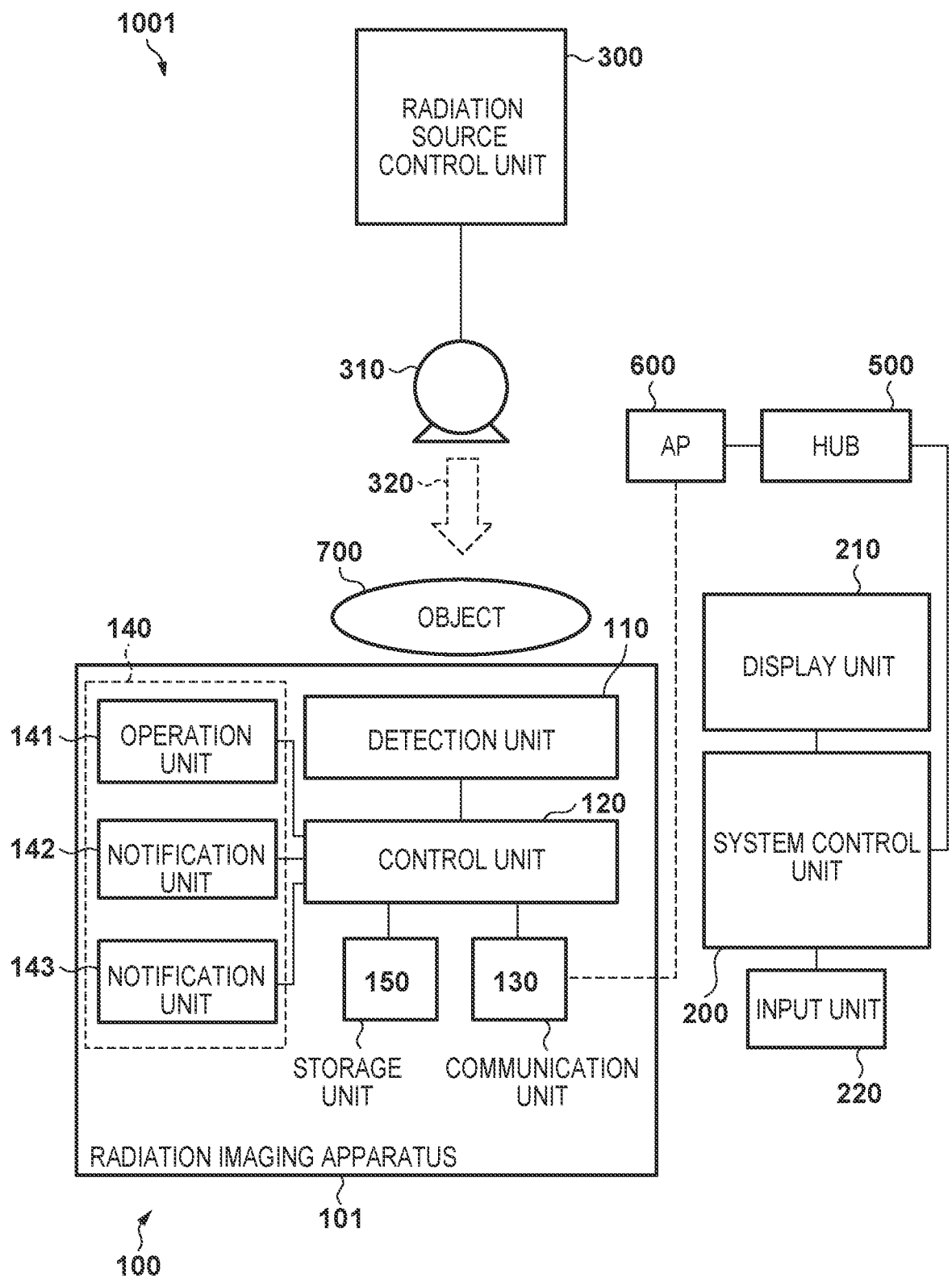
FIG. 6 is a view showing an example of the arrangement of a radiation imaging system using a radiation imaging apparatus according to an embodiment of the present invention.

The arrangement and the operation of a radiation imaging apparatus according to an embodiment of the present invention will be described with reference to FIGS. 6 to 8. FIG. 6 is a view showing an example of the arrangement of a radiation imaging system 1001 using a radiation imaging apparatus 100 according to the second embodiment of the present invention. In contrast to the radiation imaging system 1000 according to the above-described first embodiment, a radiation I/F unit 400 is not arranged and a radiation source control unit 300 is arranged independently in the radiation imaging system 1001 according to the second embodiment. Components other than these may be the same as those in the above-described radiation imaging system 1000.

In this embodiment, the radiation source control unit 300 and a radiation source 310 are independent of the radiation imaging apparatus 100 and a system control unit 200. Hence, an irradiation detection unit 114 detects the execution of radiation irradiation on the radiation imaging apparatus 100. For example, an imaging control unit 121 of the control unit 120 detects the start of radiation irradiation by using the irradiation detection unit 114 and performs control so that a flat panel detector 111 will start performing a continuous capturing operation of radiation images. A storage unit 150 not only may store image signals and various pieces of information accompanying the image signals but may also store information used for the radiation detection determination by the irradiation detection unit 114.

Figure 7A:
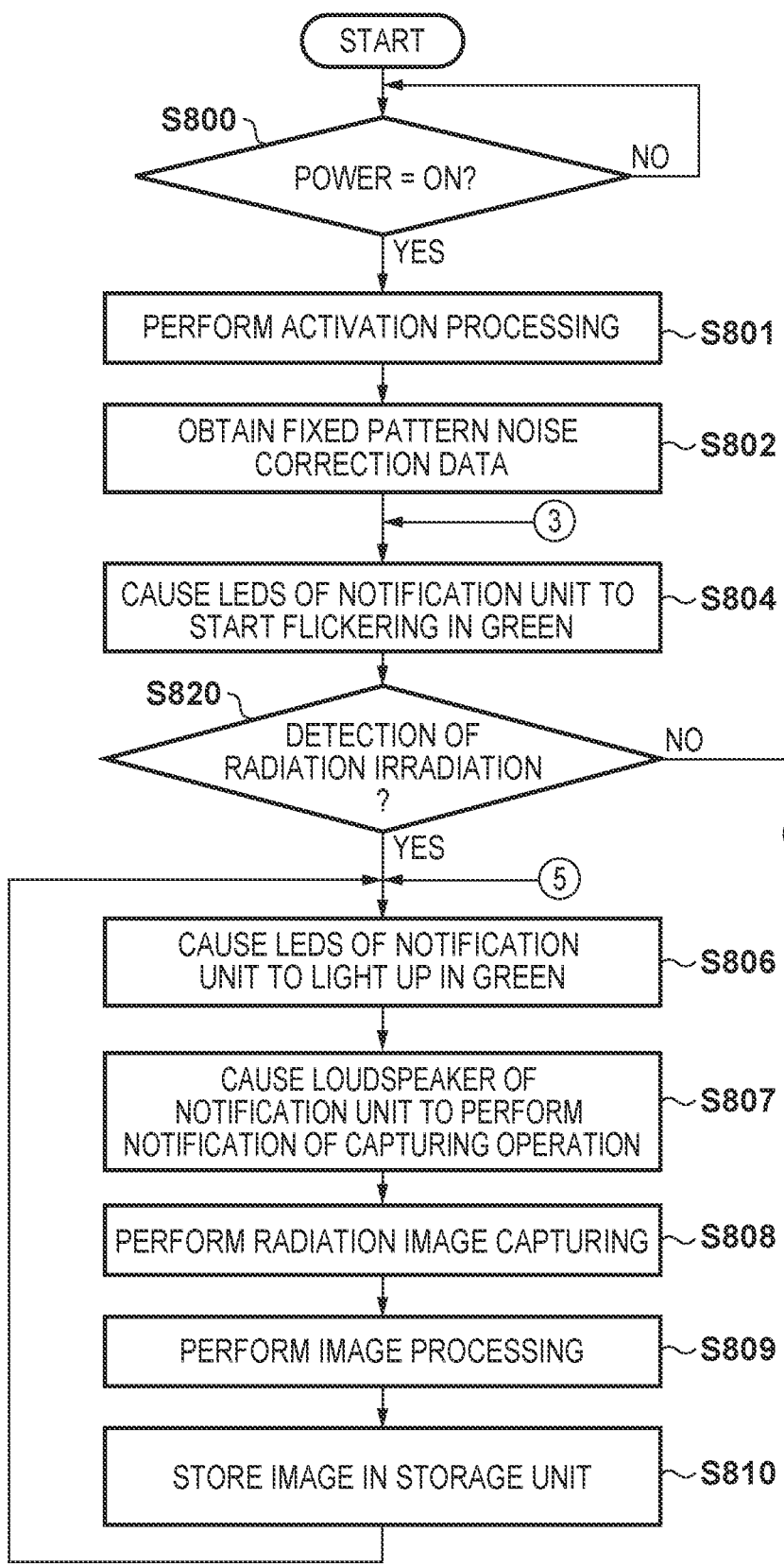
FIGS. 7A and 7B are flowcharts showing the procedure of an operation of the radiation imaging apparatus of FIG. 6.
Figure 7B:
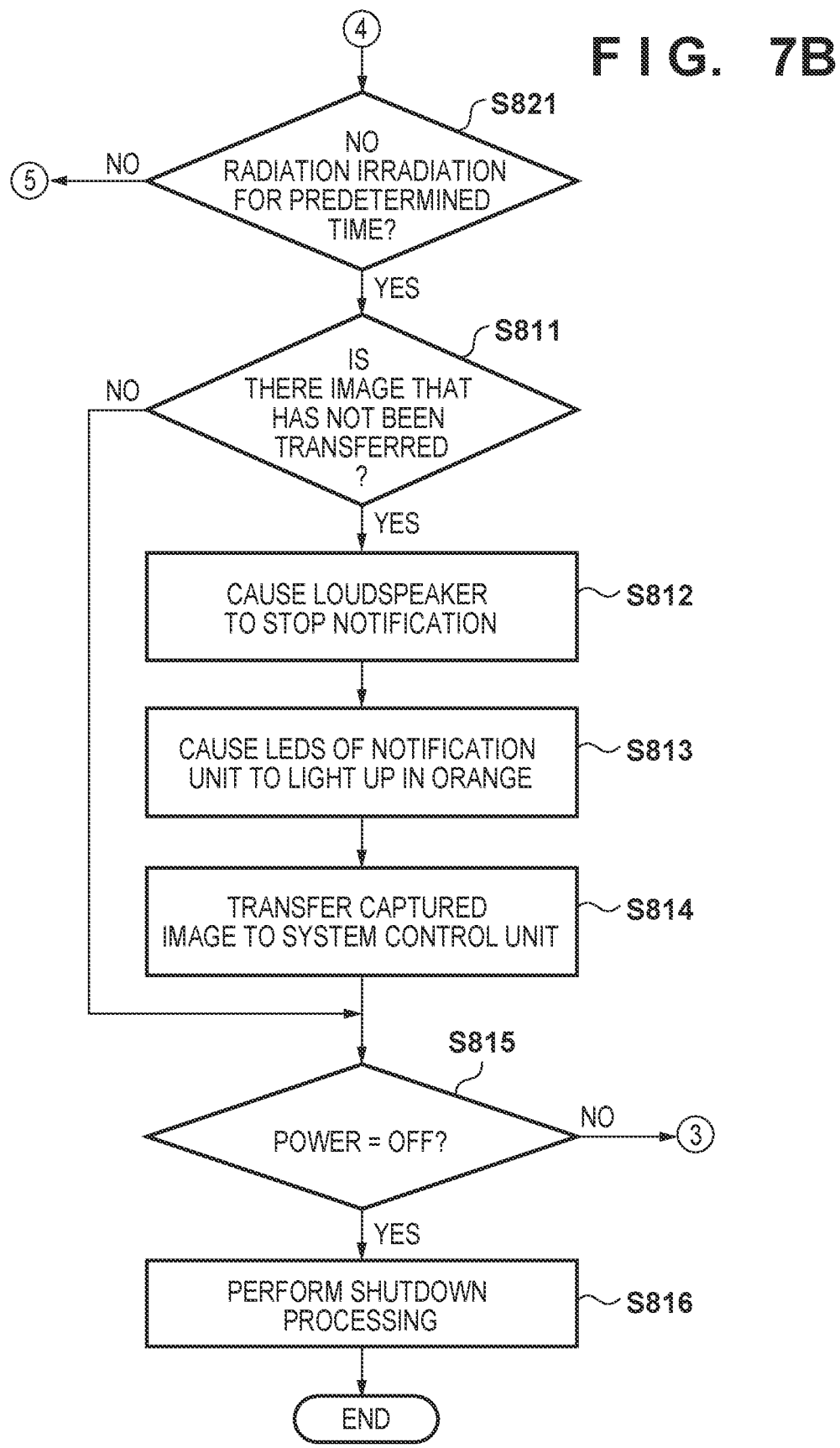

Next, the operation of the radiation imaging apparatus 100 according to the second embodiment will be described in detail with reference to the operational flowchart of FIGS. 7A and 7B. In the second embodiment, steps denoted with the same step numbers as those in the first embodiment shown in FIGS. 4A and 4B perform the same operations as those in the above-described first embodiment, and a description thereof will be omitted. The operations of steps S820 and S821 which are different from those in the first embodiment will be described in detail hereinafter.

Other than that the radiation source control unit 300 is not notified of the completion of the imaging preparation in the radiation imaging apparatus 100 in step S803, the imaging preparation processes performed from step S800 to step S804 are the same as those performed in the corresponding steps of the first embodiment. In step S804, the imaging control unit 121 of the control unit 120 completes the imaging preparation for capturing a radiation image in a detection unit 110, causes the LEDs of a notification unit 142 to flicker in green so as to notify the user of the completion of the imaging preparation, and shifts the process to step S820.

In step S820, the radiation imaging apparatus 100 determines, by the irradiation detection unit 114 arranged in the detection unit 110, whether radiation irradiation has been performed. Radiation is emitted from the radiation source 310 when the user presses an irradiation switch or a fluoroscopy pedal (not shown) connected to the radiation source control unit 300. In response to the irradiation detection unit 114 detecting the radiation irradiation by the control of the imaging control unit 121 of the control unit 120, the radiation imaging apparatus 100 shifts the process to step S806. If radiation irradiation is not detected even after a predetermined standby time has elapsed, the radiation imaging apparatus 100 shifts the process to step S821. Subsequently, the same operations as those in the first embodiment are performed in the processes of steps S806 to S810 for performing the continuous capturing operation of the radiation image.

While the radiation continues to be detected, the radiation imaging apparatus 100 performs a continuous capturing operation such as moving image capturing or tomosynthesis imaging by repetitively performing the processes of the above-described steps S820 to S810. Next, if the irradiation switch or the fluoroscopy pedal is set to OFF by the user or if the capturing operation corresponding to a frame count designated by an imaging technique defined by the user before the capturing operation has been completed, the radiation source control unit 300 performs control to stop the radiation irradiation from the radiation source 310.

After the radiation irradiation from the radiation source 310 has been stopped, the imaging control unit 121 of the control unit 120 determines in steps S820 and S821 that a series of continuous capturing operations has been completed if the irradiation detection unit 114 does not detect radiation irradiation for a predetermined time. In response to the determination that the series of continuous capturing operations has been completed, the radiation imaging apparatus 100 shifts the process to step S811. The predetermined time may be, for example, a time preset by the user. The predetermined time may also be, for example, a time obtained by doubling the radiation irradiation interval, which is preset by the user, of the continuous capturing operation. If radiation irradiation is detected again before the predetermined time has elapsed, the process shifts to step S806 and the continuous capturing operation is continued. In addition, if the process shifts to step S811, the radiation imaging apparatus 100 performs the same operations as those in the above-described first embodiment.

Figure 8:
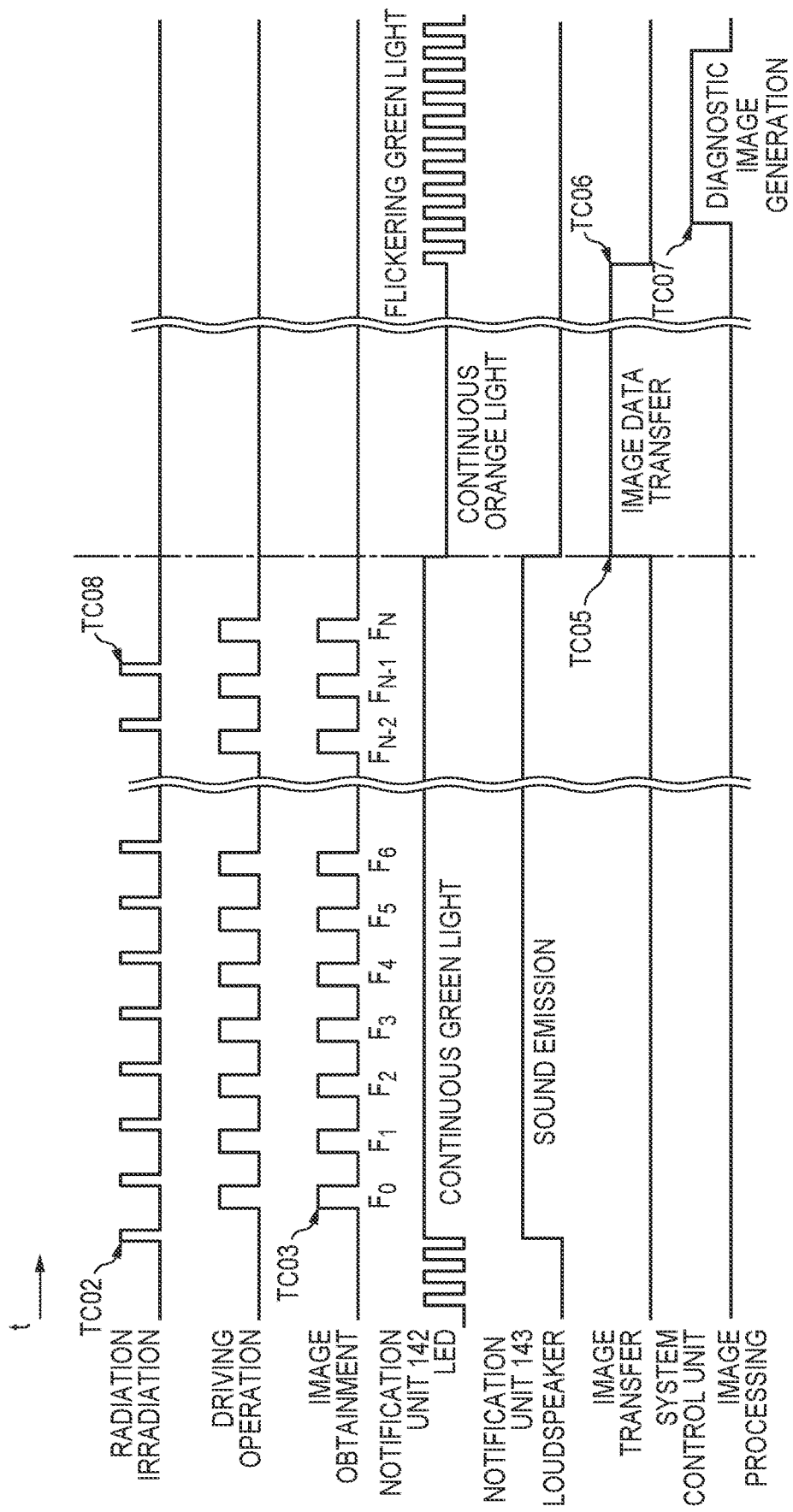
FIG. 8 is a timing chart showing the operation of the radiation imaging apparatus of FIG. 6.

FIG. 8 is a timing chart showing an example of the operation of the radiation imaging system 1001 which includes the radiation imaging apparatus 100, the radiation source control unit 300, and the system control unit 200 at the time of a continuous capturing operation according to the second embodiment. Although the procedure of the operation according to the second embodiment has been described with reference to FIGS. 7A and 7B, the operation of the radiation imaging system 1001 according to the second will be described further with reference to a timing chart.

In contrast to the above-described first embodiment, when the imaging preparation has been completed in the detection unit 110, the radiation imaging apparatus 100 causes the irradiation detection unit 114 arranged in the detection unit 110 to determine whether radiation irradiation has been performed. If the user presses the irradiation switch or a fluoroscopy pedal (not shown) of the radiation source control unit 300, radiation irradiation is started from the radiation source 310 (TC02). Although the arrangement of FIG. 8 shows that radiation irradiation is performed by performing pulse irradiation for each imaging frame to capture a radiation image, continuous radiation irradiation may be performed.

Upon detecting the radiation irradiation by the irradiation detection unit 114, the radiation imaging apparatus 100 that has received the radiation irradiation performs drive control by the control unit 120 at a predetermined timing and obtains (TC03) an image signal F0 corresponding to the radiation irradiation (TC02). The image signal obtained here is stored in a captured image storage unit 151 after undergoing necessary image processing such as fixed pattern noise correction.

Also at the timing of the detection of radiation irradiation (TC02), the radiation imaging apparatus 100 changes the LEDs of the notification unit 142 from a flickering green light state, indicating that the imaging preparation is complete, to a continuous green light state, indicating that a radiation image is being continuously captured. The radiation imaging apparatus 100 simultaneously causes the loudspeaker of a notification unit 143 to continuously emit a sound. In this manner, the radiation imaging apparatus 100 repetitively performs the continuous capturing operation while notifying the user of the ongoing continuous capturing operation by using the LEDs of the notification unit 142 and the loudspeaker of the notification unit 143 until the exposure instruction signal notification ends (TC04).

Next, if the irradiation switch or the fluoroscopy pedal is set to OFF by the user or if the capturing operation corresponding to a frame count designated by an imaging technique defined by the user before the capturing operation has been completed, the radiation source control unit 300 performs control to stop (TC08) the radiation irradiation from the radiation source 310. When the radiation irradiation is stopped (TC08), the irradiation detection unit 114 stops detecting the radiation irradiation. The control unit 120 of the radiation imaging apparatus 100 determines that the continuous capturing operation has ended if radiation is not detected for a predetermined time. In response to the determination that the continuous capturing operation has been completed, the radiation imaging apparatus 100 outputs (TC05) the image signals stored in the captured image storage unit 151 to the system control unit 200 via the imaging control unit 121 of the control unit 120, a wireless communication unit 132, and an antenna 133. During the image transfer operation, the radiation imaging apparatus 100 controls the LEDs of the notification unit 142 by the imaging control unit 121 of the control unit 120 so that the LEDs will light up in orange to indicate that the image is being transferred.

When the transfer of all of the image signals of the series of continuous capturing operations has been completed (TC06), the radiation imaging apparatus 100 changes to the imaging preparation completion state and performs control so that the LEDs of the notification unit 142 will be set to flickering green light display. As a result, the user can grasp whether the next capturing operation can be performed.

When the reception of all of the signals obtained from the continuous capturing operation has been completed (TC06), the system control unit 200 performs signal processing on the signals in the signal processing unit 201 and generates diagnostic image data (TC07). Here, for example, in the case of tomosynthesis imaging, the generation of diagnostic image data is performed by generating diagnostic image data that has been three-dimensionally reconstructed from the obtained sets of radiation image data which were captured from a plurality of positions.

In this manner, according to this embodiment, in a portable radiation imaging apparatus that has a high degree of freedom in imaging positions, can perform a continuous capturing operation, and performs wireless communication, display and a sound are used to perform notification of an ongoing continuous capturing operation such as moving image capturing or tomosynthesis imaging. As a result, a radiation imaging apparatus in which a user can easily recognize that a continuous capturing operation is being performed can be provided. In addition, even in a case in which there is no exchange of signals between the radiation imaging apparatus 100 and the radiation source control unit 300 which controls the radiation source 310, a radiation imaging system capable of capturing a radiation image can be provided.

The embodiments according to the present invention have been described above. However, the present invention is not limited to these embodiments, as a matter of course, and the above-described embodiments can be appropriately modified and combined without departing from the spirit of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-134954, filed Jul. 10, 2017 which is hereby incorporated by reference wherein in its entirety.

What is claimed is:

1. A radiographic imaging apparatus, comprising:
   a detection unit configured to generate an image signal corresponding to incident X-ray radiation;
   a notification unit configured to show a state of the radiographic imaging apparatus;
   a control unit;
   a storage unit configured to store the image signal;
   a wireless communication unit configured to transmit the image signal from the radiographic imaging apparatus wirelessly; and
   a housing in which the detection unit, the notification unit, the control unit, the storage unit and the wireless communication unit are all arranged, wherein
   the radiographic imaging apparatus is capable of performing continuous capturing operation for continuously obtaining a plurality of radiographic images based on a plurality of the image signals,
   while the radiographic imaging apparatus is performing the continuous capturing operation, the control unit stores the image signal in the storage unit and causes the wireless communication unit to wirelessly transmit the image signal from the radiographic imaging apparatus after the continuous capturing operation has ended,
   the control unit performs first control so that the notification unit notifies that the radiographic imaging apparatus performs the continuous capturing operation and second control so that the notification unit notifies that the wireless communication wirelessly transmits the imaging signal from the radiographic imaging apparatus, and
   the notification unit performs different notification in the first control and the second control.

2. The apparatus according to claim 1, wherein the control unit performs control so that the notification unit notifies that a preparation for the continuous capturing operation is completed.

3. The apparatus according to claim 1, wherein the notification unit comprises a display unit configured to indicate the state of the radiographic imaging apparatus by using at least one of a character, a figure and light.

4. The apparatus according to claim 1, wherein the notification unit comprises a sound emitting unit configured to indicate the state of the radiographic imaging apparatus by emitting a sound.

5. The apparatus according to claim 1, wherein the housing comprises an incident surface configured to be irradiated with x-ray radiation, a back surface on a side opposite to the incident surface, and side surfaces between the incident surface and the back surface,
   the detection unit comprises a detection surface on which a plurality of conversion elements configured to generate the image signal corresponding to the x-ray radiation are arranged, and
   the detection surface and the incident surface are arranged parallel to each other.

6. The apparatus according to claim 5, wherein the notification unit is arranged on the side surface.

7. The apparatus according to claim 1, further comprising an operation unit which is arranged on the housing and configured to accept an instruction from a user.

8. The apparatus according to claim 7, wherein the operation unit comprises a power button of the radiographic imaging apparatus.

9. The apparatus according to claim 7, wherein the notification unit and the operation unit are arranged on the same surface of the housing.

10. The apparatus according to claim 1, wherein the control unit is configured to receive an exposure instruction signal to cause an x-ray radiation source to perform x-ray energy irradiation, and the control unit is configured to perform control so that the detection unit starts the continuous capturing operation of the radiographic image in response to the reception of the exposure instruction signal.

11. The apparatus according to claim 1, further comprising an irradiation detection unit configured to detect the x-ray radiation irradiation on the radiographic imaging apparatus, wherein the control unit performs control so that the radiographic imaging apparatus starts the continuous capturing operation of the radiographic image in response to the irradiation detection unit detecting the x-ray radiation irradiation.

12. A radiographic imaging system comprising:
a radiographic imaging apparatus according to claim 1;
a signal processing unit configured to process an image signal from the radiographic imaging apparatus; and
an x-ray radiation source configured to perform x-ray radiation irradiation.

13. The system according to claim 12, wherein the radiographic imaging apparatus and the signal processing unit are wirelessly connected to each other.

14. The apparatus according to claim 1, wherein each of the plurality of the image signals is acquired for each imaging frame in the continuous capturing operation.

15. The apparatus according to claim 1, wherein the continuous capturing operation is moving image capturing.

16. The apparatus according to claim 1, wherein the continuous capturing operation is tomosynthesis imaging.

17. The apparatus according to claim 1, wherein the notification unit comprises a display unit configured to indicate the state of the radiographic imaging apparatus by using light, and A color of the light of the display unit in the first control is different from a color of the light of the display unit in the second control.

* * * * *